United States Patent [19]
Bergsbaken et al.

[11] Patent Number: 5,452,729
[45] Date of Patent: Sep. 26, 1995

[54] ARMBOARD COVER WITH DIAGONAL GUSSET ASSEMBLY

[75] Inventors: Brad S. Bergsbaken; Ross D. Smith, both of Tucson, Ariz.

[73] Assignee: Kimberly-Clark Corporation, Neenah, Wis.

[21] Appl. No.: 198,458

[22] Filed: Feb. 22, 1994

[51] Int. Cl.⁶ ................................................. A61B 19/00
[52] U.S. Cl. ............................................ 128/849; 128/853
[58] Field of Search .................................. 128/849–856; 5/496, 497, 499; 108/90; 150/158

[56] References Cited

U.S. PATENT DOCUMENTS

| | | | |
|---|---|---|---|
| 2,782,840 | 2/1957 | Armbrecht | 5/496 |
| 3,111,688 | 11/1963 | Barnes | 5/497 |
| 3,142,072 | 7/1964 | Goodson, Jr. | 5/497 |
| 3,856,005 | 12/1974 | Sislian | 128/132 D |
| 3,856,006 | 12/1974 | Krzewinski | 128/132 D |
| 3,862,632 | 1/1975 | Hinsek . | |
| 3,910,268 | 10/1975 | Miller | 128/132 D |
| 3,926,185 | 12/1975 | Krzewinski | 128/132 D |
| 4,027,665 | 6/1977 | Scrivens | 128/854 |
| 4,196,723 | 4/1980 | Moose, Jr. | 128/854 |
| 4,570,628 | 2/1986 | Neal | 128/853 |
| 4,586,498 | 5/1986 | Morris | 128/132 D |
| 4,664,103 | 5/1987 | Martin et al. | 128/132 D |
| 4,889,136 | 12/1989 | Hanssen | 128/849 |
| 5,074,316 | 12/1991 | Dowdy | 128/849 |

FOREIGN PATENT DOCUMENTS 0140858  5/1985  European Pat. Off. ............... 128/853

Primary Examiner—Robert A. Hafer
Assistant Examiner—Michael O'Neill
Attorney, Agent, or Firm—David J. Alexander

[57] ABSTRACT

A surgical drape and improved assembly techniques for making the same are provided. The surgical drape has a main body which includes a top edge, a bottom edge and side edges. Portions of the drape define a slit which extends from one of the side edges for a distance into the main body where it terminates. The slit is generally defined by a first slit edge and a second slit edge. A piece of material having a pair of leafs hinged about a common edge is secured to the slit. One of the edges of one of the leafs is secured to the drape near the first slit edge and one of the edges of the other leaf is secured to the drape near the second slit edge.

20 Claims, 4 Drawing Sheets

ARMBOARD COVER WITH DIAGONAL GUSSET ASSEMBLY

FIELD OF THE INVENTION

The present invention relates to surgical drapes for a number of procedures. More specifically, the present invention relates to surgical drapes having portions thereof which define armboard covers.

BACKGROUND OF THE INVENTION

As is generally known, sterile surgical drapes can be designed to greatly reduce, if not prevent, the transmission through the draping material of liquids and biological contaminates which may become entrained therein. In such surgical procedure environments, liquid and biological contaminates include, for example, operating room personnel perspiration, patient liquids, such as blood, and life support liquids, such as plasma and saline.

In the past, reusable surgical drapes were made of cotton or linen and were sterilized prior to use in the operating room. These materials however permitted transmission or "strike-through" of various liquids encountered in surgical procedures. In these instances, a path was established for transmission of bacteria and other contaminates to and from the patient. Disposable surgical drapes, which are also sterilized prior to use in the operating room, have largely replaced reusable surgical drapes, such as linen and cotton surgical drapes.

While both the selection of the fabric material and the incorporation of other materials into the draping fabric may be required to form a surgical drape suitable for providing a sufficient barrier protection to prevent the transmission of biological contaminates through the draping material, the design of such drapes is also an important consideration. Ideally, the design of the drape should be such so as to cover the patient and extend a sufficient distance below the operating room table. The extension and continuity of draping material below the surface of the operating room table is important for maintaining the sterility of the operating site.

Because the shape of operating room tables vary, so to will the design of surgical drapes vary. As the complexity of the shape of the operating room table increases, so to will the complexity of design of the surgical drape increase. For example, a surgical drape of rectangular design may be suitable for a overlying the patient reclined on a rectangular operating room table. However, the design of a surgical drape for overlying a patient reclined on a T- or L-shaped operating room table must take into consideration the additional contouring of these tables to provide for sufficient extension and continuity of draping material below the surface of the operating room table.

In the case of a T-shaped operating room table, the surgical drape may be generally T-shaped. The lower component of the T-shaped drape is generally considered as the main panel of the drape. The main panel of the drape generally covers the patients chest and lower extremity areas and overlies the main body of the operating room table. The upper component of the T-shaped drape is generally considered as the wing portion of the drape. In most instances, the wing portion of the drape overlies the patient's arms and arm boards or wings of the operating room table.

To ensure adequate coverage of both the patient and the operating room table, particularly around union of the main body of the operating room table and the arm boards, some surgical drapes, and particularly "T" shaped surgical drapes are provided with additional structure in the area around the intersection of the main panel of the drape and the wing portion of the drape. However, these drapes are generally two piece drapes, having a main panel and wing section. The wing section may include a multiple-folded sheet of draping material which is attached to the upper edge of the main panel. While this design may provide the required coverage of the patient, operating room table and arm boards, this design is labor intensive to assemble, requiring the preparation of a pre-folded sheet section followed by attachment thereof to the main panel.

Therefore, there exists a need to provide a surgical drape of simple design for use on a plurality of different shaped operating room tables, such as T or L-shaped operating room tables. The resulting drape should be of sufficient dimension for covering a reclining patient and provide the required extension and continuity of material below the surface of the operating room table in order to preserve the sterility of the operative site. The design of such a surgical drape should further permit a more efficient utilization of drape material. Additionally, the design of such a drape should also afford easy assembly, packaging and unfolding about the patient.

SUMMARY OF THE INVENTION

The present invention relates to surgical drapes and particularly to disposable surgical drapes having a main panel having a top edge, a bottom edge and two side edges. A slit having first and second slit edges is formed in a portion of the drape between the top edge and the bottom edge and extends from one of the side edges inward. A piece of material having first and second portions is secured to the main panel near the slit such that the first portion of the piece of material is secured to the main panel near the first slit edge and the second portion of the piece of material is secured to the main panel near the second slit edge. Additionally, the main panel may formed from a single piece of material having a fenestration therein.

In another embodiment of the present invention the surgical drape may be generally T-shaped. The T-shaped drape includes a first portion corresponding to the upper portion of said T, said first portion having a top edge, a left bottom edge and a right bottom edge and a pair of opposing side edges. A second portion of the T-shaped drape corresponds to the lower portion of said T, said second portion having a bottommost edge, a lower left side edge and a lower right side edge. A slit defined by first and second slit edges is formed in a portion of the drape near the intersection of the one of the bottom edges of the first portion with one of the lower side edges of the second portion. A piece of material having a first portion and a second portion is secured to the drape such that the first portion of the piece of material is secured near the first slit edge and the second portion of the piece of material is secured to second slit edge. The T-shaped surgical drape may be formed from a single sheet of material and include a fenestration therein.

The T-shaped surgical drape may further include a second slit, having first and second slit edges, formed in a portion of the drape near the intersection of the other bottom edge of the first portion with the other side edge of the second portion. A second piece of material having a first portion and a second portion is secured to the drape such that the first portion of the second piece of material is secured near the first slit edge of the second slit and the second portion of the second piece of material is secured near the second slit edge of the second slit.

The present invention also includes a method of making a surgical drape. This method includes the steps of (i) forming from a portion of sheet material suitable for use as surgical draping a generally T-shaped sheet having a first portion which corresponds to the upper portion of said T, said first portion having a top edge, a left bottom edge and a right bottom edge and a pair of opposing side edges and a second portion corresponding to the lower portion of said T, said second portion having a bottommost edge, a lower left side edge and a lower right side edge, (ii) forming a first slit defined by first and second slit edges in the drape near the intersection of one of the bottom edges of the first portion with one of the side edges of the second portion, and (iii) attaching a piece of material having first and second portions to the drape such that the first portion of the first piece of material is secured near the first slit edge and the second portion of the first piece of material is secured near the second slit edge.

This method may further include the steps of (i) forming a second slit defined by first and second slit edges in the drape near the intersection of the other bottom edge of the first portion with the other side edge of the second portion, and (ii) attaching a second piece of material having first and second portions to the drape such that the first portion of the second piece of material is secured near the first slit edge of the second slit and the second portion of the second piece of material is secured near the second slit edge of the second slit.

DETAILED DESCRIPTION OF THE INVENTION

Several terms are used herein to refer to various parts of the surgical drape as the drape is positioned in use about the operating room and patient. The "front" refers to that part of the drape which faces away from the patient. The "back" refers to that part of the drape which faces the patient.

Figure 1:
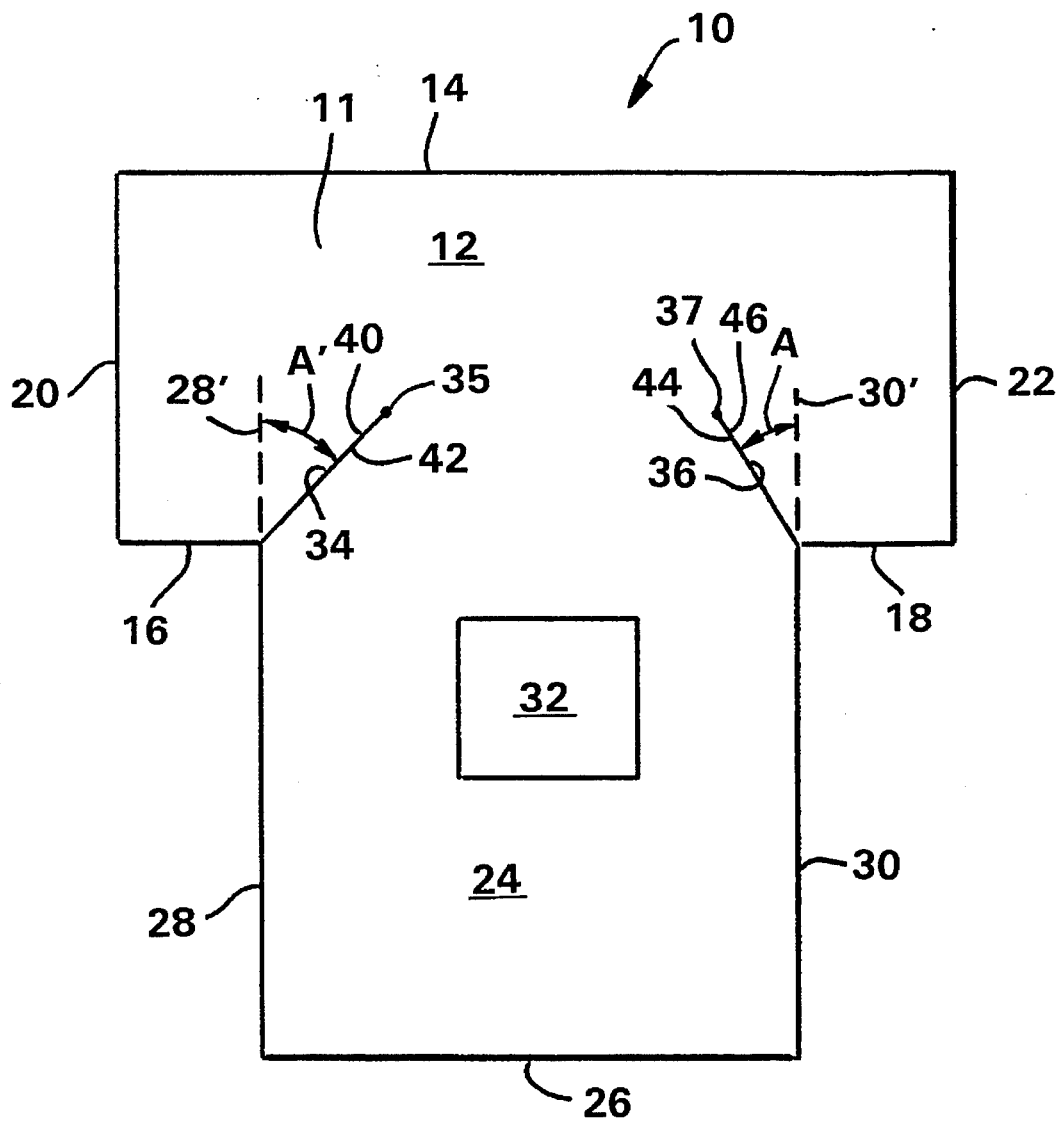
FIG. 1 is a top plan view of a T-shaped surgical drape.

Turning now to the drawings and referring first to FIG. 1, a drape 10 which is desirably formed from a single sheet of material is illustrated. The drape 10 has a front side 11 and a back side 13 (shown in FIG. 5). The drape 10 is formed in a T-shape from material suitable for use as surgical draping. Such suitable material may include a multitude of disposable and/or re-sposable materials including nonwoven and stretchable nonwoven materials. A material well-suited for use with the present invention is a three-layer nonwoven polypropylene material known as SMS. SMS is an acronym for spunbond, meltblown, spunbond. See for example, U.S. Pat. No. 4,041,203 to Brock et al.

One particular advantage is that the SMS material exhibits enhanced fluid barrier characteristics. It should be noted, however, that other disposable nonwovens as well as other materials including wovens, films, foam/film laminates and combinations thereof may be used in the present invention. It is also contemplated that the drape 10 may be coated with a liquid impervious coating to prevent fluid absorption.

The drape 10 may be made from reusable materials. Examples of suitable reusable materials include, but are not limited to, cotton, linen, polyester, woven polyester and polytetrafluoroethylene.

The T-shaped drape 10 may further be described as having a first portion 12 corresponding to the upper portion of the T and a second portion 24 corresponding to the lower portion of the T. The first portion 12 has a top edge 14, a left bottom edge 16, a right bottom edge 18 and a pair of opposing side edges 20 and 22.

The second portion 24 has a bottommost edge 26, a lower left side edge 28 and a lower right side edge 30. A fenestration 32 may also be provided in the second portion 24. It will be appreciated by those skilled in the art that the size and location of one or more fenestrations on the drape 10 will depend upon the type of surgical procedure to be preformed on the patient and the particular portion of the patients anatomy undergoing such surgical procedure.

The drape 10 further includes a pair of slits, 34 and 36. The slit 34 begins at about the intersection of the left bottom edge 16 and the lower left side edge 28. The slit 34 extends from the left side of the drape 10 for a distance towards the top edge 14 and terminates in the first portion 12 at a point 35. The slit 34 is further defined by slit edges 40 and 42.

The slit 36 begins at about the intersection of the right bottom edge 18 and the lower right side edge 30. The slit 36 extends from the right side edge of the drape 10 for a distance towards the top edge 14 and terminates in the first portion 12 at point 37. The slit 46 is further defined by slit edges 44 and 46. Both slits 34 and 36 are at about a 45° angle, indicated by letters A' and A respectively, from dash lines 28' and 30' respectively However, depending upon the shape of the operating room table and other factors, the angle of the slits 34 and 36 from dash lines 28' and 30, respectively, may vary from about 30° to 60°.

The drape 10 further includes a pair of folded triangular pieces of material 48 (FIGS. 2–5) which may be secured to the back side 13 of the drape 10. One of the triangular pieces of material is secured about one of the slits and the other triangular pieces of material is secured about the other slit. Securing of the triangular piece of material to the drape 10 may be accomplished by several conventional methods. By way of example and not limitation, these methods include taping, sewing, gluing, heat seaming, ultra-sonic bonding and other such methods familiar to those skilled in the art.

Figure 2:
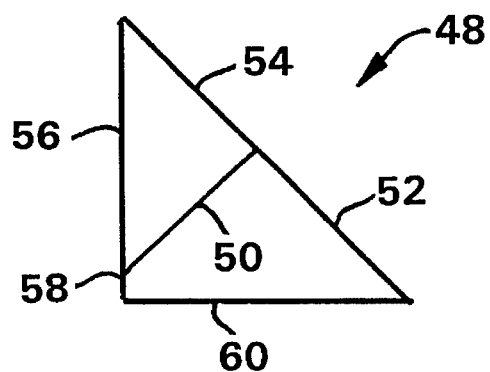
FIGS. 2–4 illustrate a folding sequence for a triangular piece of material.
Figure 3:
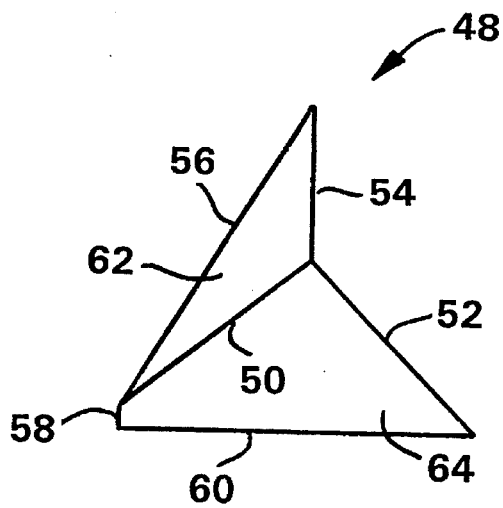
Figure 4:
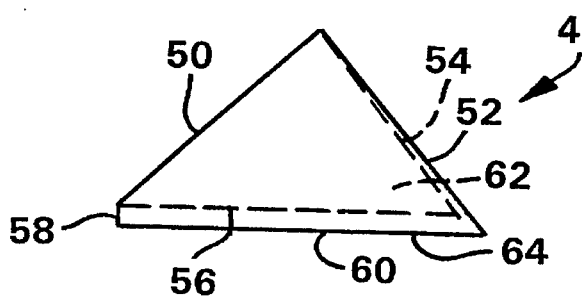

Turning now to FIGS. 2–4 a folding sequence for a triangular piece of material 48 for use on the left side of the drape 10 is illustrated. The triangular piece of material 48 has a fold line 50 and side edges 52, 54, 56, 58 and 60. The triangular piece of material 48 is folded about the fold line 50 as illustrated in FIG. 3 such that side edges 54 and 52 are substantially parallel to and abut each other and side edges 56 and 60 are substantially parallel to and adjacent each other as illustrated in FIG. 4. (In FIGS. 4 and 5, the side edges 52 and 54 are drawn in slight offset for clearity of illustration.) In this way, a pair of material leafs, 62 and 64 are formed from the triangular piece of material 48 and articulate or hinge about fold line 50. The leaf 62 is generally triangular-shaped having at least three edges and the leaf 64, overlies the leaf 62 and is generally quadrangular-shaped having at least four edges.

As previously mentioned, the folding sequence for the material 48 illustrated in FIGS. 2–4 is for installation on the left side of the drape 10. For installation on the right side of the drape 10, the material 48 is folded such that the leaf 62 overlies leaf 64.

Figure 5:
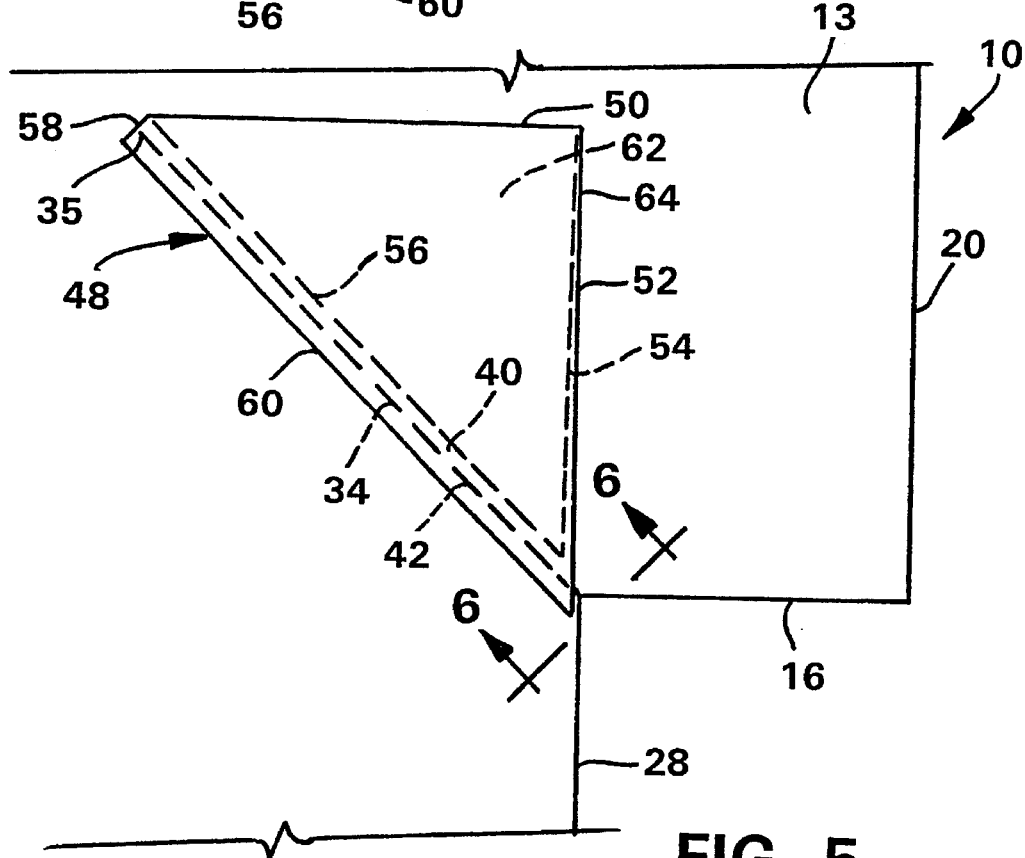
FIG. 5 is an enlarged fragmented section of the T-shaped surgical drape of FIG. 1 illustrating the orientation of the folded triangular piece of material illustrated in FIG. 4 with respect to the left back side of the T-shaped surgical drape.
Figure 6:
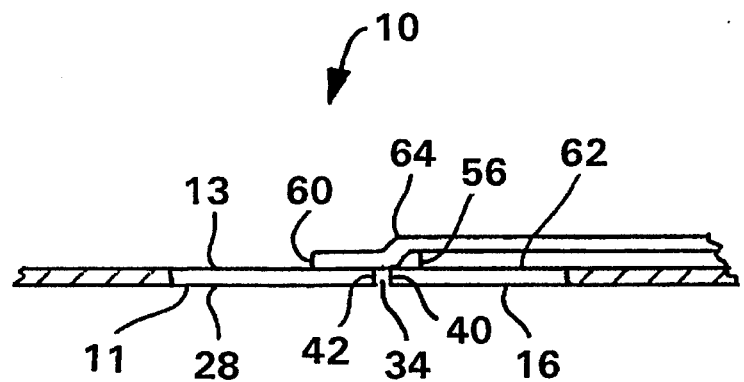
FIG. 6 is a cross sectional view through line 6—6 of FIG. 5.

FIGS. 5 and 6 illustrate the orientation of one of the triangular piece of material 48 with respect to the left back side 13 of the drape 10. Here, the triangular piece of material is positioned such that the leaf 64 overlies leaf 62. The triangular piece of material 48 is secured to drape 10 by securing the edge 60 of the leaf 64 to a portion of the drape 10 near the slit edge 42 as is most clearly illustrated in FIG. 6. The edge 56 of the leaf 62 is secured to a portion of the drape 10 near the slit edge 40. The edge 58 overlaps the termination point 35 of the slit 34 and is secured portions of the drape 10 near the termination point 35. By overlapping the termination point 35 of the slit 34, portions of the drape 10 near point 35 are strengthened, thus preventing inadvertent propagation of the slit 34. This overlap also ensures a continuity of fabric, and thus barrier continuity along the slit 34, and particularly near the termination point 35 of the slit 34.

It will be understood that the orientation and installation of the other triangular piece of material on the right back side 13 of drape 10 is substantially similar to the orientation and instillation described above for the left back side 13 of the drape 10.

Figure 7:
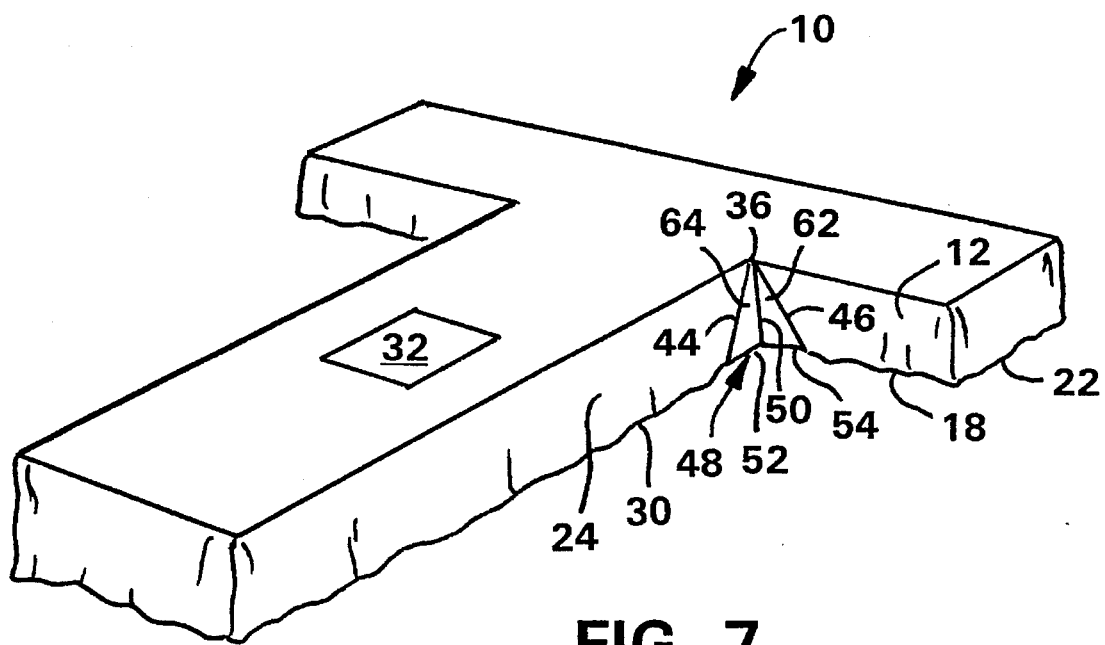
FIG. 7 is a perspective view of the T-shaped surgical drape of the present invention overlying a T-shaped operating room table.

Turning now to FIG. 7, the drape 10 is illustrated unfolded and overlying a T-shaped operating room table. It will be noted that in this overlying position, the slit edges 44 and 46 are spaced a distance apart from each other. As edges 44 and 46 separate upon the unfolding of the drape 10, the triangular piece of material 48 unfolds along fold line 50. In this way, leafs 64 and 62 provide (i) continuity between the first portion 12 and the second portion 24 along substantially the entire length of slit 36 and (ii) form fitting of the drape 10 to the adjacent portion of the operating room table.

Figure 8:
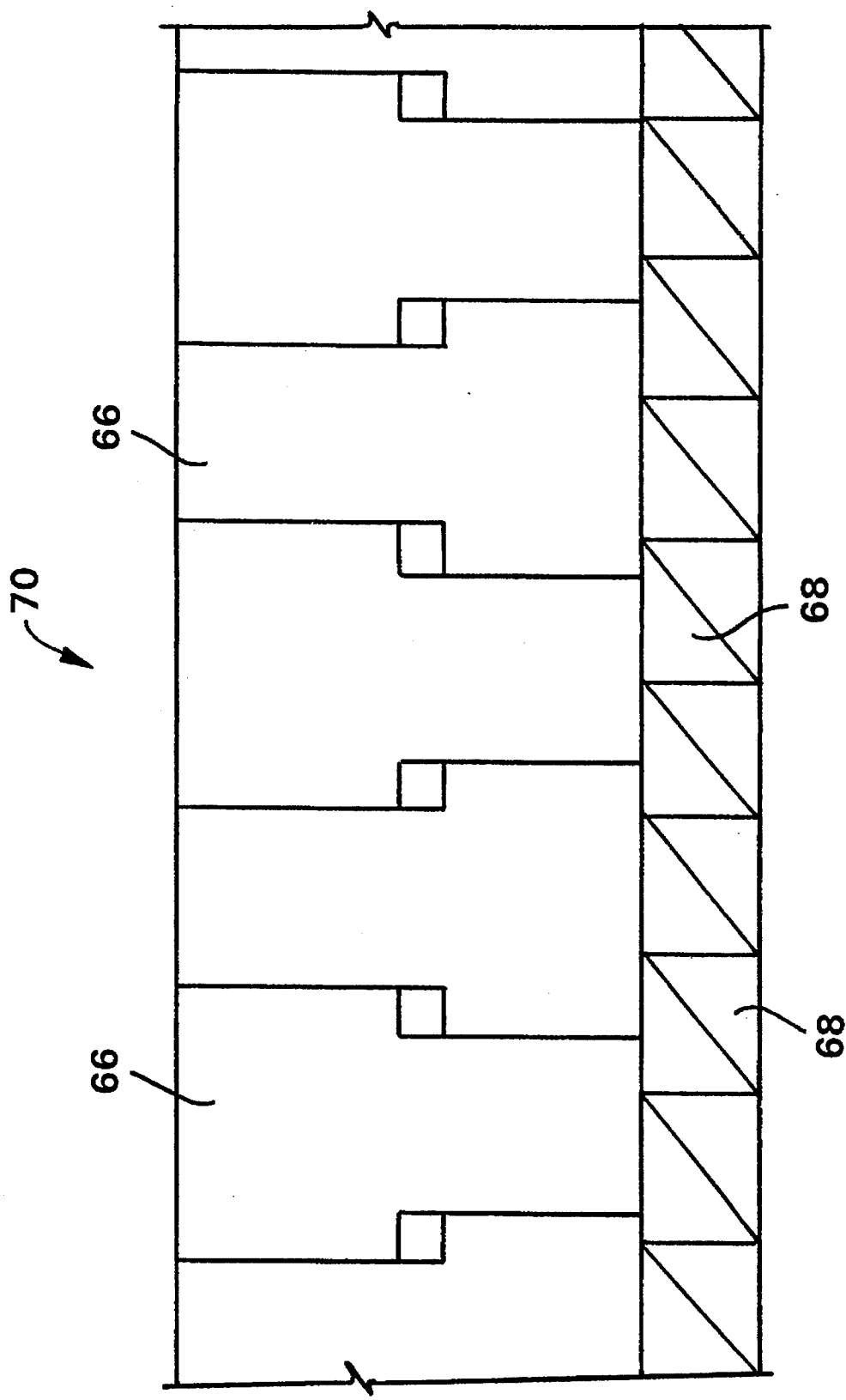
FIG. 8 is a top plan view of a continuous sheet of material illustrating a plurality of T-shaped drape cutout patterns and a plurality of triangular-shaped cut-out patterns.

Referring now to FIG. 8, a plurality of T-shaped drapes patterns 66 and triangular patterns 68 are formed on a continuous sheet of material 70. The orientation of the T-shaped drape patterns 66 and triangular patterns 68 are but one of many orientations of such patterns on the sheet of material 70. As such, FIG. 8 illustrates one of many such pattern orientations which in turn demonstrates the efficient use of material the design and method of assembly of the present invention and components thereof permit.

While the invention has been described in detail with respect to specific embodiments thereof, it will be appreciated that those skilled in the art, upon attaining an understanding of the foregoing, may readily conceive of alterations to, variations or and equivalents to these embodiments. Accordingly, the scope of the present invention should be assessed as that of the appended claims and any equivalents thereto.

We claim:

1. A surgical drape comprising:
   a main panel having a top edge, a bottom edge and two side edges; and
   wherein a portion of the drape between the top edge and the bottom edge defines a slit extending from one of the side edges for a distance, said slit further defined by first and second edges; and
   a piece of material having portions thereof defining a first leaf and a second leaf, wherein said first and second leaves articulate along a common edge, and wherein the first leaf has at least three edges and the second leaf has at least four edges and wherein the first leaf is secured to the main panel near the first slit edge and the second leaf is secured to the main panel near the second slit edge.

2. The surgical drape of claim 1 having portions defining a fenestration.

3. The surgical drape of claim 1 wherein the main panel is formed from a single sheet of material.

4. The surgical drape of claim 1 formed from a nonwoven material.

5. The surgical drape of claim 1 formed from a film material.

6. A generally T-shaped surgical drape comprising:
   a first portion corresponding to the upper portion of said T, said first portion having a top edge, a left bottom edge and a right bottom edge and a pair of opposing side edges; and
   a second portion corresponding to the lower portion of said T, said second portion having a bottommost edge, a lower left side edge and a lower right side edge; and
   wherein a portion of the drape near the intersection of the one of the bottom edges of the first portion with one of the side edges of the second portion defines a slit, said slit further defined by first and second slit edges; and
   a piece of material having portions thereof defining a first leaf and a second leaf, wherein said first and second leaves articulate along a common edge, and wherein the first leaf has at least three edges and the second leaf has at least four edges, and wherein the first leaf is secured to the drape near the first slit edge and the second leaf is secured to the drape near the second slit edge.

7. The surgical drape of claim 6 wherein the first and second portions are formed from a single sheet of material.

8. The surgical drape of claim 6 having portions thereof defining a fenestration.

9. The surgical drape of claim 6 wherein a portion of the drape near the intersection of the other bottom edge of the first portion with the other side edge of the second portion defines a second slit having first and second slit edges and a second piece of material having a first portion and a second portion wherein the first portion of the second piece of material is secured to the drape near the first slit edge of the second slit and the second portion of the second piece of material is secured to the drape near the second slit edge of the second slit.

10. The surgical drape of claim 9 wherein the second piece of material is further defined as having a first leaf and a second leaf, wherein said first and second leafs articulate along a common edge, and wherein the first leaf has at least three edges and the second leaf has at least four edges.

11. The surgical drape of claim 6 wherein the surgical drape is formed from a nonwoven material.

12. The surgical drape of claim 6 wherein the surgical drape is formed from a film material.

13. The surgical drape of claim 6 wherein the surgical drape is formed from a spunbond, meltblown, spunbond material.

14. A method of making a surgical drape comprising:
   forming from a portion of sheet material suitable for use as surgical draping a generally T-shaped sheet,
wherein the T-shaped sheet comprises;
- a first portion which corresponds to the upper portion of said T, said first portion having a top edge, a left bottom edge and a right bottom edge and a pair of opposing side edges; and
- a second portion corresponding to the lower portion of said T, said second portion having a bottommost edge, a lower left side edge and a lower right side edge;

forming a slit, defined by first and second slit edges, in the drape near the intersection of one of the bottom edges of the first portion with one of the side edges of the second portion; and attaching a piece of material having portions thereof defining a first leaf and a second leaf, wherein said first and second leaves articulate along a common edge, and wherein the first leaf has at least three edges and the second leaf has at least four edges and wherein the first leaf is secured to the drape near the first slit edge and the second leaf is secured to the drape near the second slit edge.

15. The method of claim 14 further including:

forming a second slit defined by first and second slit side edges in the drape near the intersection of the other bottom edge of the first portion with the other side edge of the second portion; and attaching a second piece of material having first and second portions to the drape such that the first portion of the second piece of material is secured near the first slit edge of the second slit and the second portion of the second piece of material is secured near the second slit edge of the second slit.

16. The method of claim 14 wherein the the piece of material is formed from a single piece of material.

17. The method of claim 14 wherein the surgical drape defines a fenestration.

18. The method of claim 14 wherein the surgical drape is formed from a nonwoven material.

19. The method of claim 14 wherein the surgical drape is formed from a film material.

20. The method of claim 14 wherein the surgical drape is formed from a foam material.

* * * * *

UNITED STATES PATENT AND TRADEMARK OFFICE
CERTIFICATE OF CORRECTION

PATENT NO. : 5,452,729

DATED : 09/26/95

INVENTOR(S) : Brad S. Bergsbaken, Ross D. Smith

It is certified that error appears in the above-identified patent and that said Letters Patent is hereby corrected as shown below:

Column 4, line 42, "respectively However" should read --respectively. However--

Signed and Sealed this

Ninth Day of January, 1996

Attest:

BRUCE LEHMAN

Attesting Officer  Commissioner of Patents and Trademarks